United States Patent [19]
Grossman

[11] Patent Number: 5,374,527
[45] Date of Patent: Dec. 20, 1994

[54] HIGH RESOLUTION DNA SEQUENCING METHOD USING LOW VISCOSITY MEDIUM

[75] Inventor: Paul D. Grossman, Burlingame, Calif.

[73] Assignee: Applied Biosystems, Inc., Foster City, Calif.

[21] Appl. No.: 3,968

[22] Filed: Jan. 21, 1993

[51] Int. Cl.$^5$ .................. C12Q 1/68; C12P 19/34; G01N 33/00
[52] U.S. Cl. .................. 435/6; 435/91.1; 935/19; 935/77; 204/180.1; 204/182.8; 204/299 R; 436/94
[58] Field of Search ............ 435/6, 91.1; 204/180.1, 204/299 R, 182.8; 935/19, 77; 436/94

[56] References Cited

U.S. PATENT DOCUMENTS 5,089,111  2/1992  Zhu et al. .................. 204/180.1
5,126,021  6/1992  Grossman .................. 204/180.1

FOREIGN PATENT DOCUMENTS

0497480A1  1/1992  European Pat. Off. .

OTHER PUBLICATIONS

Chiari, M., et al., "Capillary electrophoresis of macromolecules in 'syrupy' solutions: Facts and misfacts," *Electrophoresis* 13:690–697 (1992).
Cohen, A. S., et al., "Rapid separation and purification of oligonucleotides by high-performance capillary gel electrophoresis," *Proc. Natl. Acad. Sci. USA* 85:9660–9663 (1988).
Cohen, A. S., et al., "Separation and analysis of DNA sequence reaction products by capillary gel electrophoresis," *J. Chromatography* 516:49–60 (1990).
Guttman, A., et al., "Analytical and Micropreparative Ultrahigh Resolution of Oligonucleotides by Polyacrylamide Gel High-Performance Capillary Electrophoresis," *Anal. Chem.* 62:137–141 (1990).
Heiger, D. N., et al., "Separation of DNA restriction fragments by high performance capillary electrophoresis with low and zero crosslinked polyacrylamide using continuous and pulsed electric fields," *J. Chromatography* 516:33–48 (1990).
Huang, K. C., et al., "Capillary Array Electrophoresis Using Laser-Excited Confocal Fluorescence Detection," *Anal. Chem.* 64:967–972 (1992).
Huang, X. C., et al., "Capillary gel electrophoresis of single-stranded DNA fragments with UV detection," *J. Chromatography* 600:289–295 (1992).
Huang, X. C., et al., "DNA Sequencing Using Capillary Array Electrophoresis," *Anal. Chem.* 64:2149–2154 (1992).
Mathies, R. A., and Huang, X. C., "Capillary array electrophoresis: an approach to high-speed, high-throughput DNA sequencing," *Nature* 359:167–169 (1992).
Sudor, J., et al., "Pressure refilled polyacrylamide columns for the separation of oligonucleotides by capillary electrophoresis," *Electrophoresis* 12:1056–1058 (1991).
Swerdlow, H., and Gesteland, R., "Capillary gel electrophoresis for rapid, high resolution DNA sequencing," *Nucleic Acids Research* 18(6):1415–1419 (1990).
Swerdlow, H., "Capillary gel electrophoresis for DNA sequencing. Laser-induced fluorescence detection with the sheath flow cuvette," *J. Chromatograhy* 516:61–67 (1990).

*Primary Examiner*—Margaret Parr
*Assistant Examiner*—Bradley L. Sisson
*Attorney, Agent, or Firm*—Peter J. Dehlinger; Vincent M. Powers; Paul D. Grossman

[57] ABSTRACT

A DNA sequencing method for use in sequencing a DNA target sequence up to 300 bases, preferably up to 500 bases or greater in length, by electrophoretically separating a mixture of single-stranded DNA sequencing fragments in a capillary tube. The method employs an aqueous denaturing solution comprising between about 4 and about 7 weight percent linear polyacrylamide molecules having an average molecular weight of between about 20 and about 100 kDa. The low-viscosity of the solution allows rapid loading and reloading of such solution into the capillary tube.

17 Claims, 4 Drawing Sheets

28.2 mins.

58.7 mins.

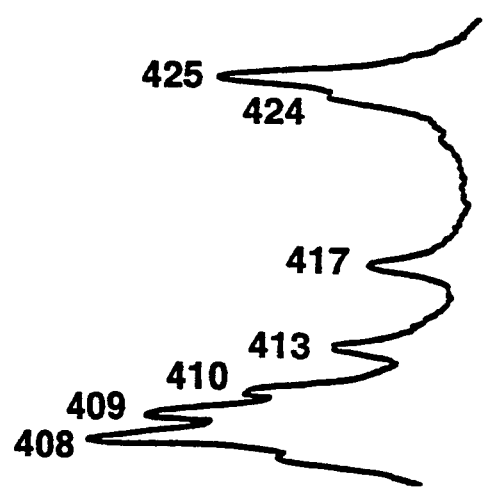
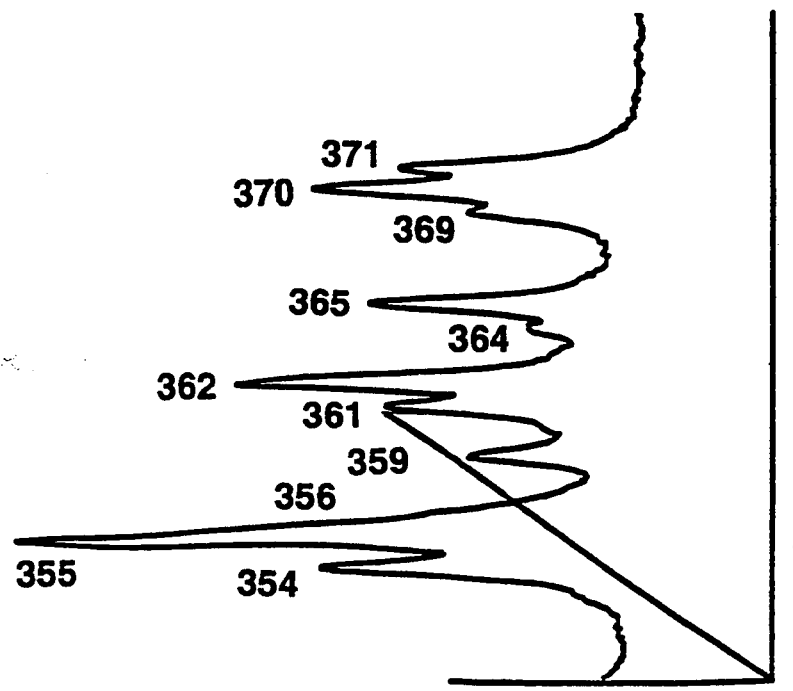
Fig. 2D
Fig. 2C

HIGH RESOLUTION DNA SEQUENCING METHOD USING LOW VISCOSITY MEDIUM

FIELD OF THE INVENTION

The present invention relates to DNA sequencing methods based on separation of DNA fragments in a DNA fragment mixture by capillary electrophoresis.

REFERENCES

Altria, K. D., et al., Electrophoresis 11:732 (1990).

Applied Biosystems, *Model 370A DNA Sequencing System/Tag Polymerase Technical Manual*, Applied Biosystems, Foster City, Calif. (1989).

Ausubel, F. M., et al., *Current Protocols in Molecular Biology*, John Wiley & Sons, Inc., Media, Pa.

Bergot, J. B., et al. PCT Publication No. WO 91/05060, published Apr. 18, 1991.

Cobb, K. A., et al., Anal. Chem. 62:2478 (1990).

Cohen, A. S., et al., J. Chrom. 516:49 (1990).

Grossman, P. D., and Colburn, J. C., Eds., *Capillary Electrophoresis*, Academic Press, Inc., San Diego, Calif. (1992).

Guttman et al., Anal. Chem. 62:137 (1990).

Heiger, D. N., et al., J. Chrom. 516:33 (1990).

Hiemenz, P. H., *Principles of Colloid and Surface Chemistry*, 2nd Ed., Marcel Dekker, Inc., NY (1986).

Huang, X. C., et al., Anal. Chem. 64:967 (1992a).

Huang, X. C., et al., Anal. Chem. 64:2149 (1992b).

Huang, X. C., et al., J. Chrom. 600:289 (1992c).

Karger, B. L., and Cohen, A. S. U.S. Pat. No. 4,865,706 (1989).

Mathies, R. A., and Huang, X. C. Nature 359:167 (1992).

Maxam, A. M., and Gilbert, W., Proc. Natl. Acad. Sci. USA 74:560 (1977).

Pentoney, S. L., et al., J. Chrom. 480:259 (1989a).

Pentoney, S. L., et al., Anal. Chem. 51:1642 (1989b).

Pentoney, S. L., et al., Electrophoresis 13:467 (1992).

Sambrook, J., et al., *Molecular Cloning*, 2nd Ed., Cold Spring Harbor Laboratory Press, NY (1989).

Sanger, F., et al., Proc. Natl. Acad. Sci. USA 74:5463 (1977).

Smith et al., Nucl. Acids Res. 13:2399 (1985).

Sudor, J., et al., Electrophoresis 12:1056 (1991).

Swerdlow, H, et al., Nucleic Acids Res. 18:1415 (1990a).

Swerdlow, H., et al., J. Chrom. 516:61 (1990b).

BACKGROUND OF THE INVENTION

Electrophoresis is widely used for fractionation of a variety of biomolecules, including DNA species, proteins, peptides, and derivatized amino acids. One electrophoretic technique which allows rapid, high-resolution separation is capillary electrophoresis (CE) (Grossman and Colburn, 1992). Typically, CE employs fused silica capillary tubes whose inner diameters are between about 10–200 microns, and which can range in length between about 5–100 cm or more.

One use for CE that has received much attention has been in the separation and identification of DNA sequencing fragments. Such separations have been carried out previously using slab gel configurations requiring painstaking preparation of crosslinked polyacrylamide matrices between glass plates. More recently, methods have been described for carrying out such separations by CE, providing the advantages of shorter separation times, reduced sample sizes, potential automation of sample loading, and potentially higher resolution of sample peaks.

Guttman et al. (1990) have reported single-base separation of polynucleotides containing on the order of 160 bases by CE using crosslinked polyacrylamide gels containing 3–6% T and 5% C.

Cohen et al. (1990) have demonstrated use of CE with a crosslinked polyacrylamide gel (3% T, 5% C) to separate DNA sequencing fragments differing in length by a single base from 18 to about 330 bases in total length.

Swerdlow et al. (1990a) have compared the separation of DNA sequencing fragments achieved by CE with that achieved by slab gel electrophoresis using identical crosslinked polyacrylamide matrices (6% T, 5% C). The separations afforded by CE were said to be 3-fold faster and to provide 2.4-fold better resolution and 5-fold better separation efficiency than provided by a conventional slab gel configuration.

Although crosslinked polyacrylamide matrices such as above have been shown to be useful in DNA sequencing analysis, certain limitations have remained. One limitation has been that bubbles can form in the polyacrylamide matrix during polymerization in the capillary tube, compromising peak resolution and necessitating rejection of some acrylamide-filled tubes following polymerization (Swerdlow, 1990a,b).

Another limitation has been the formation of bubbles near the injection end of the capillary tube during electrophoresis of the sample (Swerdlow, 1990b).

A third limitation has been that at high voltages, electroosmosis can occur, leading to extrusion of the gel matrix from the tube. To counter such extrusion, crosslinked matrices have been covalently attached to the inside wall of the tube (Karger et al., 1989). However, such covalent linkage can lead to the formation of voids in the matrix due to contraction during polymerization or electrophoresis (Grossman et al., 1992, at pp. 140–142).

A fourth limitation, in DNA sequence analysis, has been the fouling of the capillary inlet by the sequencing template. Accumulation of a large, essentially immobile template at the inlet can limit the degree of resolution achievable with subsequently loaded samples, thereby limiting use of the capillary to a few uses at most.

Another limitation has been that, when polymerization of the matrix is carried out in the capillary tube, the polymerization procedure must be performed individually for each tube and typically requires a significant delay (e.g., overnight polymerization) before the capillary can be used for electrophoresis.

Linear (non-crosslinked) polyacrylamide matrices have also been found useful in the separation of DNA fragments. Heiger et al. (1990) have shown that linear polyacrylamide matrices containing 6, 9, 12% T were useful in the separation by CE of restriction fragments ranging in size from about 75–12,000 basepairs in length (non-denaturing conditions), and further, that a higher % T (e.g., 9% T) was useful in resolving, under denaturing conditions, a mixture of polydeoxyadenylate fragments ranging from 40–60 bases in length. The authors suggested that polymerization of the polymer matrix be performed inside the capillary tube to obtain high viscosity and to minimize the difficulties of handling viscous solutions.

Sudor et al. (1991) reported separation of DNA fragments using linear polyacrylamide solutions containing 3-10% T (weight percent of total acrylamide) and 7M urea. Polyacrylamide-filled capillary tubes were prepared by forming the polyacrylamide solution outside of the tube and then forcing the polymerized solution into the tube by syringe, while taking care not to break the syringe due to excessive pressure. Comparison of CE separations performed with solutions containing 3, 5, and 10% T showed that 10% T gave the best resolution of oligonucleotide test fragments (poly-dC) 10 to 36 bases in length.

More recently, Mathies, Huang, and coworkers (Huang et al., 1992a,b,c; Mathies et al., 1992) have described a linear polyacrylamide matrix (9% T containing 7M urea) for DNA sequence analysis by CE. The matrix is said to typically allow sequencing of up to 300-350 bases per capillary (Huang et al., 1992b), and as high as 500 bases beyond the primer (Huang et al., 1992a). The highly viscous matrix is polymerized in the capillary tube and is said to be physically stable, allowing multiple (e.g., three or four) sample injections.

Ideally, a matrix for use in separating DNA sequencing fragments should (i) provide single-base resolution for DNA sequencing fragments of 300 bases in length, preferably 500 bases in length, or greater, and (ii) have a sufficiently low viscosity to allow rapid filling and re-filling of the capillary tube.

SUMMARY OF THE INVENTION

The present invention provides an improved method and apparatus for achieving single-base resolution of DNA sequencing fragments, by providing a low-viscosity medium that can readily be loaded into and removed from a capillary electrophoresis tube.

In one aspect, the invention includes an improved automated method of determining the nucleotide sequence of a target polynucleotide, in which DNA fragments in a DNA sequencing mixture are separated by size in a capillary electrophoresis tube. The improvement includes separating the DNA fragments in an aqueous denaturing solution comprising between about 4 and about 7 weight percent polyacrylamide molecules having an average molecular weight of between about 20 and about 100 kDa. The solution viscosity allows filling of a capillary electrophoresis tube by applying a low pressure differential across the tube, e.g., no more than about 100 psi. After fragment separation, the polyacrylamide solution is removed from the tube and fresh aqueous denaturing solution is introduced into the tube by applying a pressure differential across the ends of the tube.

In another aspect, the invention includes an improved method of determining the nucleotide sequence of a target polynucleotide, wherein DNA fragments in a DNA sequencing mixture are separated by size. The improvement includes separating the DNA fragments by capillary electrophoresis in an aqueous denaturing solution comprising between about 4 and about 7 weight percent linear polyacrylamide molecules.

The linear polyacrylamide molecules preferably have an average molecular weight between about 20 kDa and about 100 kDa, more preferably about 55 kDa.

The separation medium (polymer solution) for use in the methods of the invention is effective to achieve a single-base resolution for fragments of at least about 300 bases in length, and preferably at least 500 bases in length, although the method can be used for smaller selected ranges, e.g., for achieving single-base resolution for fragments in the range of about 30 to about 100 or 200 bases in length.

These and other objects and features of the invention will become more fully apparent when the following detailed description of the invention is read in conjunction with the accompanying drawings.

BRIEF DESCRIPTION OF THE DRAWINGS

FIGS. 2A-2E show selected time segments of a single electropherogram obtained by the method of the invention with a mixture of DNA sequencing fragments. The fragments were generated by the Sanger method and terminate at their 3'-ends with the dideoxy form of cytidine. The length of each fragment is indicated by the number at the top of each peak.

DEFINITIONS

Figure 1:
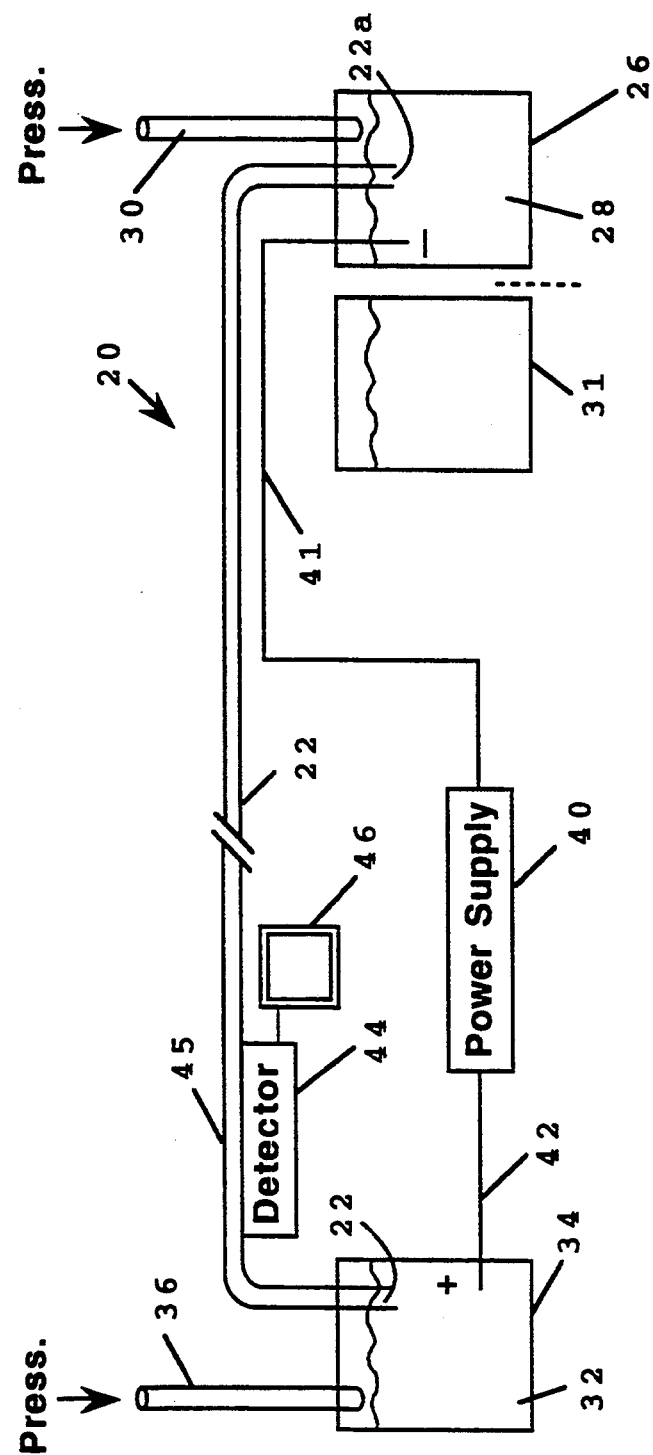
FIG. 1 shows a schematic view of a capillary electrophoresis apparatus in accordance with the invention.

"Acrylamide" and "acrylamide monomer" refer to a structure having the form $NH_2C(=O)CR_1=CR_2R_3$, where $R_1$ is hydrogen, and $R_2$ and $R_3$ can be hydrogen or a methyl group.

"Polymer" is used in its traditional sense of a large molecule composed of smaller monomeric subunits covalently linked together to form a chain.

"Linear polyacrylamide" or "linear polyacrylamide polymer" refers to a polymer formed from acrylamide monomers in the absence of a crosslinking agent.

"Crosslinked polyacrylamide" refers to a polymer formed from acrylamide monomers in the presence of a crosslinking agent (e.g., bis-acrylamide) to produce a 3-dimensional, covalently crosslinked gel.

"Aqueous denaturing solution" refers to an aqueous solution containing a denaturing agent (e.g., urea) at a concentration effective to maintain polynucleotides in a single-stranded state largely or entirely devoid of secondary structure.

The term "polymer solution" refers to any solution containing linear polyacrylamide molecules of the invention, i.e., having an average molecular weight of between about 20 kDa and about 100 Kda. The polymer solution may contain a denaturing agent as defined in the preceding paragraph.

"Average molecular weight" refers to the number-average molecular weight $(M_n)$ of a sample population made up of polymer species having a multiplicity of molecular weights. This quantity is defined by the equation:

$$M_n = (\Sigma n_i \times MW_i)/\Sigma n_i$$

where $n_i$ indicates the number of molecules of species i, and $MW_i$ is the molecular weight of species i.

"Electrophoretic mobility" refers to the steady-state velocity induced per unit field strength for a selected molecular species. Electrophoretic mobility can be measured in terms of the time required for a molecular species to pass a particular point in the tube, or in terms of distance of a molecular species from a reference point along the length of the tube at a selected time. "Relative electrophoretic mobility" refers to the electrophoretic mobility of a molecular species in comparison to that of another molecular species.

The term "DNA sequencing fragments" refers to DNA polynucleotides generated for the purpose of obtaining sequence information about a selected DNA target sequence. Such fragments can be generated enzymatically, e.g., by the Sanger dideoxy method, or chemically, e.g., by the approach of Maxam and Gilbert, for example. In addition, the fragments may originate from a single sequencing reaction (e.g., a dideoxy sequencing reaction performed in the presence of dideoxycytidine triphosphate), or from more than one sequencing reaction (e.g., from four different dideoxy sequencing reactions which include suitably labeled 5'-primers to identify the 3'-terminal base of each fragment).

DETAILED DESCRIPTION OF THE INVENTION

The present invention provides a linear polyacrylamide preparation having an average molecular weight between about 20 kDa and about 100 kDa, which is useful in a sieving medium (polymer solution) for separating polynucleotides, and particularly, DNA sequencing fragments. For electrophoresis, the polymer solution contains the linear polyacrylamide at a concentration of between about 4 and about 7 weight %, along with a denaturant and a selected buffer for controlling the pH of the solution.

The polymer solution of the invention can be introduced into the capillary tube by applying a small pressure differential across the two ends of the tube. The polynucleotide sample is introduced into one end of the capillary tube and an electric field is applied across electrode reservoirs in which the ends of the tube have been immersed. As the polynucleotide fragments move through the electric field, they are fractionated on the basis of length by differential migration through the sieving matrix established by the polymer solution.

While the polymer solution of the invention is particularly useful in determining a contiguous nucleotide sequence in a target polynucleotide (DNA or RNA) molecule, other uses of the solution include detection of differences (e.g., mutations) between two or more sequences, assessment of the purity of synthetic oligonucleotides, and resolution and sizing of restriction fragments.

I. Capillary Electrophoresis Apparatus

FIG. 1 is a simplified schematic view of a capillary electrophoresis system 20 (Applied Biosystems, Foster City Calif.) suitable for practicing the method of the invention. The system includes a capillary tube 22 having a length preferably between about 10–200 cm, typically less than about 100 cm, and an inner diameter (i.d.) of preferably between about 10–200 $\mu$m (microns), typically about 50 $\mu$m. In the embodiment shown, the tube is supported in a horizontal position and has downwardly bent end regions. The capillary tube is of a type that permits suppression of electroosmosis during electrophoresis (e.g., such that electroosmosis is below about $2 \times 10^{-5}$ cm$^2$/sec-V), and which interacts minimally or not at all with the sample. One preferred capillary tube is a fused silica tube having an inner diameter of 50 $\mu$m (available from Polymicro Technologies, Phoenix, Ariz.), the inner surface of which is chemically coated as detailed in section II.B below.

More generally, the capillary tube may be any tube or channel capable of supporting a column of polymer solution, preferably having an inner diameter of 200 $\mu$m or less. For example, the tube may take the form of a channel formed in a glass slide or the like.

A cathodic reservoir 26 in system 20 contains an electrolytic polymer solution 28, described further in the sections which follow. The cathodic end of the tube, indicated at 22a, is sealed within reservoir 26 and is immersed in the polymer solution, as shown, during electrophoresis. Second tube 30 in reservoir 26 is connected to a finely controlled air pressure system (not shown) which can be used to control the pressure in the head space above the polymer solution, e.g., for loading polymer solution into the tube by positive pressure. The pressure system is able to generate a pressure differential across the ends of the capillary tube of about 100–300 psi or less.

Additionally, the air pressure system can include a vacuum system for drawing solution through the capillary tube.

A sample reservoir 31 in system 20 contains the sample mixture to be loaded into the cathodic end of the tube. Preferably, the sample has been dissolved in a denaturing solution which maintains the sample polynucleotides in single-stranded form. For example, a dried DNA sample from a sequencing reaction can be dissolved in a mixture of 1 volume of 5 mM aqueous EDTA, and 12 volumes of formamide, and heated at 90° C. for 2 minutes prior to sample loading. The sample and cathodic reservoirs may be carried on a carousel or the like, for placement at a position in which the cathodic end of the tube can be immersed in the reservoir fluid. Although not shown here, the carousel may carry additional reservoirs containing, for example, solutions for cleaning and flushing the tube between electrophoretic runs, or different polymer solutions.

The opposite, anodic end of the tube, indicated at 22b, is immersed in an anodic electrolyte solution 32 contained in an anodic reservoir 34. A second tube 36 in reservoir 34, analogous to tube 30 in reservoir 26, can be included to control the pressure above solution 32, e.g., for loading polymer solution into the tube, just as with tube 30 in reservoir 26. Typically, the compositions of electrolyte solutions 28 and 32 are identical to the polymer solution in the capillary tube.

For sample loading and subsequent sample separation by electrophoresis, the filled capillary tube and electrode reservoirs are preferably configured so that there is little or no net liquid flow through the tube. This can be effected by keeping the surfaces of the electrode reservoir solutions at the same height, or by controlling the atmospheric pressures above the two solutions.

A high voltage supply 40 in the system is connected to the cathodic and anodic reservoirs as shown, for applying a selected electric potential between the two reservoirs. The power supply leads are connected to platinum electrodes 41, 42 in the cathodic and anodic reservoirs, respectively. The power supply may be designed for applying a constant voltage (DC) across the electrodes, preferably at a voltage setting of between 6 kV and 20 kV.

Detector 44 in the system is positioned adjacent the anodic end of the tube, for monitoring sample peaks migrating through an optical detection zone 45 in the tube. Typically, the capillary tubing has been treated to remove a small region of exterior polyimide coating (in the case of a polyimide-coated capillary tube) to create a small window. The detector may be designed for UV or visible absorption detection, and/or for fluorescence emission detection or radioisotope detection, for example.

Fluorescence emission detection is preferably carried out at one or more selected excitation wavelengths which are adjustable between about 240–600 nm, depending on the fluorescent species associated with the sample molecules. Typically, the detector employs an argon laser as an excitation source. Preferably, a confocal optical arrangement is used (e.g., Huang et al., 1992, page 968). For recording electrophoretic peaks, the detector is connected to an integrator/plotter 46, which may take the form of a computer for data storage on a magnetic medium or the like.

Radioisotope detection may be accomplished by the use of a modified HPLC isotope detector for $^3H$ or $^{14}C$ (Radiomatic Instruments & Chemical Co., Inc., Meriden, Conn.). For detection of $^{32}P$-labeled peaks, a semiconductor or scintillation-based radioisotope detector device may be used (Pentoney et al., 1989a, pages 2625-2629, 1989b pages 259-270). A detector configured for gamma-ray detection may also be used (e.g., Altria et al., 1990, pages 732-734).

In operation, the capillary tube is thoroughly washed by flushing suitable rinsing solutions through the tube by applying positive pressure to the head space above the appropriate solution reservoir. Alternatively, the capillary can be washed manually by syringe. In the practice of the present invention, the polymer-containing electrolyte solution itself can be used to flush the system between sample runs. If a cleaning solution different from the polymer electrolyte solution is used, the tube is then flushed with several volumes of the polymer solution.

The sample is then loaded into the cathodic end of the tube, typically by electrokinetic injection. The cathodic end of the tube is placed in the sample solution, and a brief, high voltage pulse is applied across the two ends of the tube (e.g., 6 kV for 5 seconds). The tube end is then returned to the solution in cathodic reservoir 26, and a separation voltage (e.g., 12 kV) is applied until the desired number of fragment peaks have passed through the detection zone.

For automated electrophoresis of multiple samples, the apparatus may be adapted to include an array of capillary tubes and suitable detection means for simultaneous monitoring of sample migration in the tubes. By such an arrangement, the same sample or a number of different samples can be analyzed in parallel using such an array.

II. Linear Polyacrylamide Compositions

As indicated above, the present invention is based on the discovery that a low-viscosity solution containing a selected concentration of linear polyacrylamide molecules in a selected molecular weight range is useful for providing single-base resolution of large DNA sequencing fragments in capillary electrophoresis. The polymer solutions of the invention are significantly lower in viscosity than the linear polyacrylamide media that have previously been used for high resolution separation of DNA sequencing fragments.

II.A Preparation of Linear Polyacrylamide

The linear polyacrylamide molecules of the present invention are characterized by an average molecular weight between about 20 kDa and about 100 kDa.

The average molecular weight of the polymer population can be adjusted by a number of factors. In one approach, the conditions of polymerization are changed in order to effect changes in the MW of the final polymer population. The average molecular weight can be decreased by (1) increasing the reaction temperature, (2) increasing the ratio of radical initiator to acrylamide monomer, or (3) increasing the amount of chain transfer reagent. Transfer reagents that can be used include lower alkyl alcohols, with isopropanol being preferred.

Example 1 describes a procedure for preparing a linear polyacrylamide preparation in accordance with the invention. In the procedure, a mixture of isopropanol (6.55 ml) in water (222 ml) is stirred at 35° C. for 10 minutes while being de-gassed with helium. Acrylamide (25 g) is then added and allowed to fully dissolved. After dissolution of the acrylamide, polymerization is initiated by the addition of TMED (N,N,N',N'-tetramethylethylenediamine) and APS (ammonium persulfate), to final concentrations of about 0.05% (w:v and v:v for TMED and APS, respectively), and polymerization is allowed to continue for 90 minutes with vigorous stirring.

Preferably, the polymer solution is dialyzed in 12-14 kDa MW-cutoff dialysis tubing against multiple changes of buffer over several days to remove low molecular weight reactants. Following dialysis, the polymer solution is lyophilized, providing dried polymer in about 40% yield.

A second method for adjusting the average MW of a polymer is by fractionating the polymer into different MW fractions followed by isolation and purification. An aqueous solution of polymer is fractionated by a size-dependent chromatographic separation (such as gel permeation chromatography), or by fractional precipitations using a water miscible solvent such as methanol.

Conveniently, the molecular weight distribution of the polymer thus obtained is represented as a number-average molecular weight as defined earlier above. The average molecular weight can be determined using gel permeation chromatography according to procedures which are well known in the art (e.g., see Hiemenz, 1986, pp. 42-49). In brief, the retention times of a number of polyacrylamide standards of known molecular weight composition are determined to establish a standard curve that correlates molecular weight with elution time. The standard curve is used to determine the average molecular weight of the sample based on elution time. An exemplary molecular weight determination is provided in Example 2.

II.B Polymer Solution

For separating single-stranded polynucleotides, the polymer solution includes a denaturant at a concentration effective to maintain polynucleotides in a single-stranded state that is largely or entirely devoid of secondary structure. Typically, urea at a concentration of 7-8M is employed. In general, the polymer solution used for separating DNA fragments in the present invention has a viscosity between about 10 and about 300 centipoise, as measured at 30° C.

The solution also includes a buffer for maintaining the pH of the solution at a selected value between about 4-9. For any given buffer species used, there exists an optimum concentration for maximum sample peak resolution. Band-broadening may occur at a too low concentration (low ionic strength) or at too high a concentration (high ionic strength). In general, zwitterionic buffers improve resolution and reduce background UV absorbance variations.

For achieving high resolution of single-stranded polynucleotides, the polymer of the invention is present in the polymer solution at a concentration between about 4 and about 7 weight %.

According to an important aspect of the invention, the polymer solution of the invention is readily flowable, allowing easy, rapid filling and refilling of the capillary tube. Preferably, the viscosity is sufficiently low (about 10 to about 300 centipoise, measured at 30° C.) to allow filling of a 50 cm×50 μm i.d. capillary tube within 30 minutes using a pressure differential across the tube of less than about 100 psi, preferably less than 50 psi. Alternatively, by use of a syringe and application of gentle pressure, the polymer solution of Example 4 can be loaded into such a capillary in less than 60 seconds. The feature of rapid filling is particularly amenable to an automated capillary electrophoresis procedure for DNA sequence analysis.

Table 1 below shows calculated fill times for the above capillary tube at polymer viscosities ($\eta$) from 10 to 300 centipoise.

TABLE 1

| $\eta^*$ | $t_{fill}$ (min) |
|---|---|
| 300 | 23 |
| 100 | 7.7 |
| 50 | 3.9 |
| 25 | 2.0 |
| 10 | 0.8 |

*length = 50 cm, pressure differential = 100 psi, i.d. = 50 μm.

II.C Preparation and Filling of Capillary Tube

The capillary tube for use in the invention is of a type that permits suppression of electroosmosis during electrophoresis (e.g., such that electroosmosis is below about $2 \times 10^{-5}$ cm$^2$/sec-V), and which interacts minimally or not at all with the sample. Preferred capillary tubes are those having internal diameters of less than about 200 microns, preferably less than about 100 microns, and more preferably within the range of about 25-50 microns, although sizes below 25 microns are also contemplated.

Typically, the tube is composed of fused silica having an exterior polyimide coating to confer structural rigidity. Electroosmosis can be suppressed by masking the negative charge along the inner silica surface of the tube. Such masking can be accomplished by application of a chemical coating, which binds to the inner surface covalently or noncovalently, using approaches known in the art. Details of a procedure for preparing a suitable covalent coating based on the method of Cobb et al. (1990, page 2479) are provided in Example 3. The selected coating should be stable under the separation conditions employed, and preferably affords single-base resolution for fragments up to 300 bases in length, preferably up to 500 bases in length, or greater, for at least one day of multiple runs (e.g., through 5 consecutive runs performed over a period of about 8 hours).

In the coating procedure described in Example 3, a fused silica capillary tube is flushed with 1.0M NaOH and then coated using a three step procedure. In the first step, the silica surface of the inner wall is chlorinated using thionyl chloride. Prior to chlorination, the tube is flushed with about 80 column volumes of dry, distilled tetrahydrofuran (THF) to dry the inner wall surface. After removal of residual THF (e.g., by helium stream), a solution of thionyl chloride containing a trace amount of dimethylformamide (DMF) is passed through the tube to chlorinate the silica surface. The reaction is continued overnight by joining the two ends of the tube to each other and incubating the tube in an oven at 55° C.

In the second step, the tube is flushed with several column volumes of dry, distilled THF to remove the thionyl chloride solution, and then flushed with a 1M solution of vinyl magnesium bromide (Grignard reagent) in THF (~100 column volumes over about 5 hours). The tube is heated intermittently with a heat gun to facilitate the reaction. After the 5 hour flushing step, the ends of the tube are again joined to each other and heated overnight at 70° C.

In the third step, the surface vinyl groups are reacted with acrylamide. The capillary is first conditioned by sequential flushing with THF (to remove the Grignard solution), methanol, and water. The tube is then flushed over 30 min with freshly prepared aqueous polymerization solution containing 3% (w:v) acrylamide monomer, 0.1% (v:v) TMED, and 0.1% (w:v) APS. Following this step, the tube is flushed with water and then dried by helium stream. The dried coated tube may be stored at −20° C. until use.

Loading of polymer solution into a capillary tube for sample separation is conveniently accomplished by syringe, or by application of positive pressure in the head space above a reservoir solution in which one end of the capillary tube is immersed. For loading by syringe, one end of the capillary tube is connected to a syringe, and polymer solution is loaded into the tube using gentle pressure on the syringe plunger. A 50 cm×50 μm i.d. capillary tube can be filled within 60 seconds by syringe, without trapping bubbles in the tube.

Preferably, for use in an automated CE apparatus, the tube is loaded or reloaded with polymer solution by application of positive pressure in the head space above a reservoir solution. In this approach, one end of the capillary tube (e.g., the anodic end) is immersed in polymer solution contained in a reservoir (e.g. in the anodic reservoir of a CE apparatus as in section I above). The head space above the reservoir solution is sealed off from the outside atmosphere by suitable sealing means adapted to allow one end of the capillary tube to pass into the reservoir solution. The sealing means further allows access of the reservoir head space to a controllable gas pressure source (e.g., a compressed-gas cylinder having suitable regulating means). By applying a positive pressure to the head space above the anodic solution, a pressure differential across the tube ends is created, driving anodic reservoir solution into the tube. As indicated above, the low-viscosity solution used in the invention can be introduced rapidly into the capillary tube at low pressure, e.g., 100 psi or less. The pressure differential is maintained until solution exits the cathodic end of the tube, at which time the cathodic end is immersed in the cathodic solution.

As mentioned earlier, the filled capillary tube and electrode reservoirs are preferably configured so that there is little or no net liquid flow through the tube. This can be effected by keeping the surfaces of the electrode reservoir solutions at the same height, or by controlling the atmospheric pressures above the two solutions.

III. Electrophoresis Method

The polynucleotide sample which is to be electrophoretically separated is prepared by standard methods. Typically, the sample is a mixture of DNA sequencing fragments derived from one or more sequencing reactions. The two primary techniques for DNA sequencing are chemical methods (e.g., Maxam and Gilbert, 1970), and enzymatic methods (e.g., Sanger et al., 1977). Routine protocols for both techniques are widely available (e.g., Sambrook, Chapter 13, 1989). Although the techniques differ in approach, both produce populations of polynucleotides (sequencing fragments) which begin at a defined 5'-terminal base site and end randomly at a selected base or a combination of selected bases. (The four standard nucleotide bases for DNA are deoxyadenylate, deoxycytidylate, deoxyguanylate, and thymidylate, abbreviated as A, C, G, and T, respectively). Typically, the fragments include a reporter label (referred to interchangeably as "reporter" or "label") for enhanced detection, and, where appropriate, for distinguishing fragments which terminate at a selected base from other fragments which terminate at one or more different selected terminal bases. Any label suitable for either or both purposes may be used, with a fluorescent label being preferred. For example, the fragments may be labeled by use of a fluorescent or radio-labeled 5'-primer, by use of fluorescent-labeled dideoxy-terminal nucleotides (e.g., Bergot et al., 1991, pages 1-20), or by use of radioactive nucleotides (e.g., $^{35}$S-labeled dATP).

Usually, the dideoxy (enzymatic) method of Sanger et al. is used. In this method, a DNA template is annealed to a 5'-primer oligonucleotide in solution by brief heating (e.g., 60° C. for 10 minutes) of the solution followed by slow cooling over 20-30 minutes to 4°-20° C. Preferably, the primer includes a fluorescent label which is covalently bound to the 5'-terminal base in the primer. Suitable fluorescent dyes and labeling methods which may be used are described in U.S. Pat. No. 4,855,525, which is incorporated herein by reference. The template-primer solution is then incubated in the presence of (i) selected concentrations of the four standard nucleotide bases (ii) a selected concentration of the dideoxy form of the selected terminal base, and (iii) a DNA polymerase. The polymerase-catalyzed reaction is allowed to proceed for a selected time and is then stopped by suitable means (e.g., by quenching the reaction in cold ethanol). Note that if desired, one or more of the standard bases can be substituted with a selected nucleotide analog; e.g., c7dGTP in place of dGTP, for avoiding peak compression. The action of DNA polymerase is effective to generate labeled DNA fragments which begin with the (labeled) 5'-primer sequence, terminate at their 3'-ends with the dideoxy form of the selected terminal base, and which are complementary in sequence to the template DNA.

Where a sequence of contiguous bases is to be determined, it is preferable that four separate sequencing reactions be performed, one for each standard base. Moreover, it is also preferred that for each reaction, a different label is used, such that fragments formed in each sequencing reaction can be distinguished from the fragments formed in the other three reactions. Classes of spectrally resolvable fluorescent dyes suitable for this purpose have been described (e.g., U.S. Pat. No. 4,855,525; Smith et al., 1985, pages 2399-2412), thereby allowing fragments from the four sequencing reactions to be electrophoretically separated in the same lane (migration path). Four "universal" M13 5'-primers which are labeled respectively with four spectrally resolvable fluorescent dyes (designated FAM, JOE, TAMRA, and ROX) are commercially available from Applied Biosystems.

The DNA sequencing fragments produced in each sequencing reaction are usually isolated from cold ethanol solution by centrifugation. After the pellet has been washed with cold 70% ethanol, the resultant pellet is dried briefly, e.g., by vacuum centrifuge for 3 minutes, and is then ready for electrophoretic analysis. Alternatively, the sample is stable in this dried form for several months if stored in the dark at −20° C.

Prior to being loaded in the capillary tube, the dried DNA fragment sample is resuspended in a denaturing solution and heated briefly to convert all of the DNA fragments to single-stranded form. For example, the denaturing solution can consist of a mixture of 1 volume of 5 mM aqueous EDTA, and 12 volumes of formamide. After suspension in the denaturing solution, the sample is heated at 90° C. for 2 minutes, and then loaded into the cathodic end of the polymer solution-filled capillary tube, typically by electrokinetic injection as above. If fragments from more than one reaction are to be loaded on the capillary tube, the fragments from the reactions are preferably mixed before loading.

FIGS. 2A-2E show time segments of an electropherogram obtained with a mixture of sequencing fragments terminating at C (3'-end), generated as described in Example 4. In these figures, fluorescence intensity (in arbitrary units) is plotted as a function of elution time past the detector. The length of each fragment, which was determined from the known sequence of the m13mp18 (+) strand, is indicated at the top of each peak. The spacing of elution times of the fragments correlated closely with the known sequence positions of the cytidylate residues.

Figures 2A, 2B:
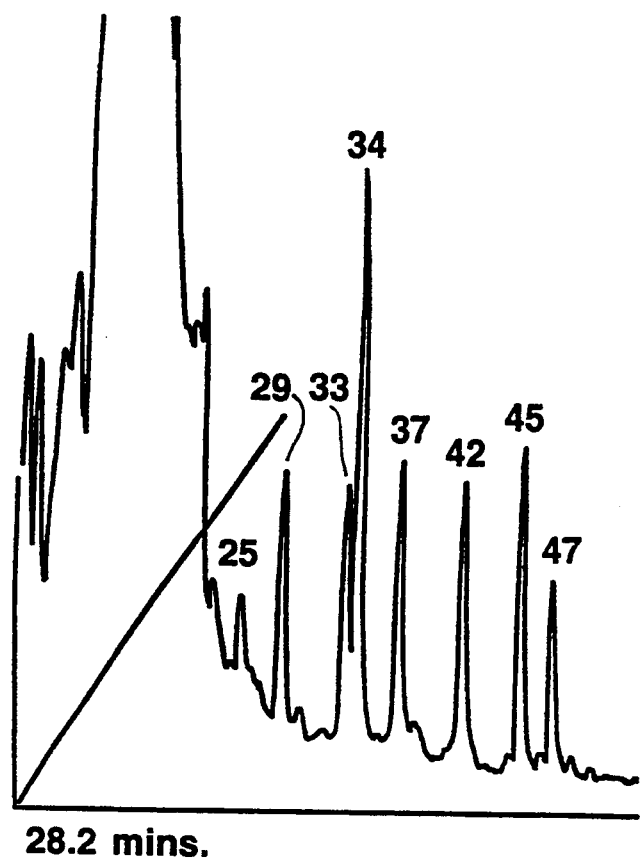
Figure 2E:
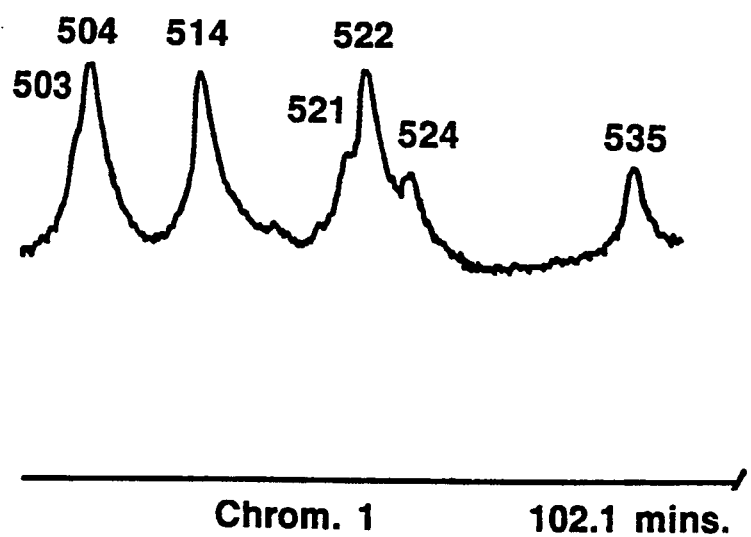

FIG. 2A shows the separation of fragments ranging in length from about 20 to 50 bases. As can be seen, peaks differing in length by a single base were nearly baseline resolved. FIG. 2B shows the separation of fragments ranging in length from about 220 to 260 bases. Again, single-base resolution was achieved. FIG. 2C shows the separation of fragments ranging in length from about 350 to 371 bases. As can be seen, fragments greater than 300 bases in length are well resolved. FIGS. 2D and 2E show the separation of fragments in the size ranges of about 405 to 425 bases (FIG. 2D) and about 500 to 525 bases (FIG. 2E), respectively. These figures show that fragments having lengths up to 400 bases, 500 bases, or greater, can be resolved in the method.

Electrophoretic separation of the DNA sequencing sample from Example 4 was also carried out using a conventional slab gel configuration (Applied Biosystems Model 370A DNA Sequencing System, Applied Biosystems, Calif.). A crosslinked matrix containing 4% T and 5% C was used. The electropherogram which was obtained showed peak resolution comparable to that obtained by the capillary electrophoresis analysis just described. More importantly, the relative peak intensities were essentially the same as those found by capillary electrophoresis, demonstrating that the variable peak heights in FIGS. 2A-2E are attributable to the DNA sample (i.e., to the actual amount of each fragment in the sample), and not to a defect in the separation method.

After the mobilities of the desired number of sequencing fragments have been recorded, electrophoresis is stopped, and the polymer solution in the capillary tube can be replaced. For example, positive pressure in the head space above the anodic reservoir solution can be used to drive several column volumes of new polymer solution through the capillary tube. The other end of the capillary can be directed to a waste collector for disposal. The newly filled capillary tube is then ready for separating another sample.

IV. Utility

The polymer composition and method of the invention are particularly useful for obtaining sequence information about a selected polynucleotide target sequence. In one aspect, knowledge of the sequence of a contiguous stretch of nucleotides may be desired, in which case sequencing fragments are prepared in four different sequencing reactions, as described in section III above. Where the fragments from all four reactions are to be separated in the same migration path (the same capillary tube), the fragments from each reaction are labeled so as to be distinguishable from the fragments from the other three reactions. Although using four spectrally resolvable labels is preferred, other labeling schemes can be used, e.g., a binary scheme using two distinguishable labels (Huang et al., 1992b, pages 2151-2154). In the approach of Huang et al., the four sequencing reactions are distinguished using the following four label combinations, where A and B represent the two labels used: label A only, label B only, both A and B, neither A nor B. As another alternative, a single label which is used at four different amplitudes can be used (Pentoney et al., 1992, pages 467-474).

In another aspect, the method of the invention can be used for determining whether two target sequence regions from two different samples are identical. Here, the expected sequence is already known, and at least one sequencing reaction is carried out with each target sequence using sequence-identical primers that contain distinguishable labels. The terminal base is selected to be the same in each of the two reactions. The sequencing fragments from each reaction are loaded together on a capillary tube, and the resultant electropherogram (corrected for mobility differences caused by the respective labels, if necessary) is inspected to determine whether the elution profiles representing the two target sequences are the same. Where a single site mutation in the target sequence is known to occur, and the selected terminal base is chosen to be the base characteristic of the mutation, the method provides rapid assessment of whether such a mutation is present.

The method of the invention can also be used for determining a sequence "signature" of a target sequence, wherein the relative spacing between bases which belong to a selected base-type (e.g., to cytidylate) is recorded as an identifying feature (qualitative or definitive) of the target sequence. Preferably, the relative spacing is determined in the presence of a standard fragment mixture of known lengths, to allow correction for run-to-run variability in electrophoretic mobility.

The uses described above are presented strictly for the purpose of illustration, as many variations within the spirit and scope of the invention are possible.

From the foregoing, it can be appreciated how the objects of the invention are met. The polymer solution of the invention can provide single-base resolution of DNA fragments ranging from about 30 to about 500 bases in length or greater. The low-viscosity of the solution allows easy replacement of the solution in the tube following separation of a sample mixture, thereby avoiding the problems of sample buildup and ghost peaks from previous runs. Further, use of the capillary tube for multiple sample separations reduces capillary consumption while also streamlining the automation of multiple sample analyses.

The following examples illustrate, but are in no way intended to limit the present invention.

EXAMPLES

Materials and Methods. Chemicals were obtained from Aldrich Chemical Co. (Milwaukee, Wis.) or from commercial sources of comparable quality.

Example 1

Preparation of Linear Polyacrylamide

For the following procedure, stock solutions of TMED (N,N,N',N'-tetramethylethylenediamine, 10% v:v in water) and APS (ammonium persulfate, 10% w:v in water) were prepared.

To a 500 ml Erlenmeyer flask maintained at 35° C. in a water bath was added 222 ml water and 6.55 ml isopropanol. The solution was stirred for about 10 minutes, with helium being bubbled into the solution. Acrylamide (25 g) was then added (~1.5M final concentration). When the acrylamide had fully dissolved, 1.25 ml each of the TMED and APS stocks above were added, and polymerization was allowed to continue for 90 min with vigorous stirring, yielding a solution having a honey-like consistency.

The polymer solution was dialyzed against 5 changes of water (3.5 liters each) over three days at 4° C. using a 12-14 kDa cutoff dialysis membrane (Spectra/por #2, Spectrum Medical Industries, Los Angeles, Calif.). Following dialysis, the polymer solution was lyophilized, yielding 9.58 g dried polymer.

Example 2

Molecular Weight Determination

The molecular weight of the polymer material from Example 1 was determined by gel permeation chromatography. Samples and standards were run on a Waters 590 Solvent Delivery System (Milford, Mass.) equipped with two Waters Ultrahydrogel Linear columns connected in series, and a Waters R401 Differential Refractometer for peak detection. Other conditions: injected sample, 80 μl of ~4 mg/ml stock; flow rate, 0.6 ml/min; mobile phase, 100 mM potassium phosphate, pH 7.0.

Properties of four non-ionic linear polyacrylamide standards (Polysciences, Inc., Warrington, Pa.) used in the molecular weight determination are shown in Table 2:

TABLE 2*

| Standard | $M_n$ |
|---|---|
| 1 | 465,306 |
| 2 | 141,000 |
| 3 | 44,400 |
| 4 | 13,700 |

*$M_n$, number-average molecular weight.

From the elution times and known average molecular weights of these standards, a calibration curve was established. Based on the calibration curve, the polymer sample from Example 1 was determined to have a number-average molecular weight of 55 kDa.

Example 3

Preparation of Coated Capillary Tube

Fused-silica capillary tubing (TSP 050375, Part #2000017) having the following dimensions was from Polymicro Technologies, Tucson, Ariz.: length=20 m, i.d.=50 μm, o.d.=361 μm, outer polyimide layer thickness=16 μm. From this tubing, a 5 meter segment was removed, and a series of 8 evenly spaced 2 mm windows were formed in the tubing by burning off the polyimide coating with a hot wire. The windows were spaced about 55 cm apart so that 8 or 9 capillary tubes, each containing a window 40 cm from the inlet and 15 cm from the outlet, could be prepared from the 5 meter segment.

Prior to the coating procedure below, the tubing was flushed manually by syringe with a 1.0M solution of NaOH, followed by automated flushing with water using a syringe pump (Model 351, Orion Research, Cambridge, Mass.).

The inner wall of the capillary tube was chemically coated in three steps using a modification of the procedure of Cobb et al. (1990, page 2479).

In the first step, the silica surface of the inner wall was activated using thionyl chloride ($SOCl_2$). Prior to chlorination, the tube was flushed over a 4 hour period with dry, distilled tetrahydrofuran (THF) using the above syringe pump, to dry the inner wall surface. A 2 ml gas-tight syringe was used, with the flow rate set to "0.4", and size set to "5". The total volume of THF passed through the tube was about 800 µl (about ~80 column volumes). Residual THF was then expelled manually from the tube using a helium stream, and a mixture of dimethylformamide (DMF, 10 µl) in $SOCl_2$ (2 ml) was passed through the tube by syringe pump, as for THF above (~4 hours, ~800 µl). The ends of the tube were then joined with a tight plastic sleeve, and the tube was incubated in an oven overnight at 55° C.

In the second step, the chloride-activated inner wall of the tube was reacted with vinyl magnesium bromide ("Grignard reagent"). The chloride-activated tube was first flushed by syringe pump with dry, distilled THF (1 hour, ~300 µl) to remove the $SOCl_2$ solution, and then flushed with a 1M solution of the Grignard reagent in THF (syringe pump, 2 ml syringe, ~1 ml over 5 hours). The tube was heated intermittently with a heat gun to facilitate the reaction. After the 5 hour wash period, the ends of the tube were joined again by a tight plastic sleeve, and the capillary tube, still containing the Grignard solution, was incubated overnight at 70° C.

In the third step, the vinyl-coated inner wall was reacted with acrylamide to impart an acrylamide coating. The capillary was first flushed by syringe pump with THF to remove the Grignard solution (1 ml syringe, ~200 µl over 20 min), with methanol (~150 µl), and then with water (~200 µl). The tube was then flushed over 30 min with a freshly prepared polymerization solution (1 ml) containing 300 µl of 10% w:v acrylamide in water, 700 µl of water, 1 µl of TMED, and 10 µl of a 10% (w:v) aqueous solution of APS. The tube was then flushed with water (100 µl), dried by helium stream for 1.5 hours, and stored in a −20° C. freezer until use.

Example 4

Sequence Analysis of DNA a Polynucleotide

The capillary electrophoresis apparatus was equipped with a high voltage power supply (Gamma High Voltage Research, Inc., Ormand Beach, Fla.) and a Model 600 Data Analysis System for data collection (Applied Biosystems, Inc., Foster City, Calif.). A capillary tube prepared as in Example 3 (50 µm internal diameter, 55 cm length, 40 cm to detector) was arranged to connect an anodic reservoir to an electrically grounded cathodic reservoir.

Detection of labeled polynucleotides was carried out using a fluorescence detector positioned adjacent a 2 mm long window formed in the surface of the capillary tube, 40 cm from the cathodic end, as in Example 3. Excitation light from an argon ion laser (Model 221-40MLA, Cyonics, San Jose, Calif.) was passed through a 0.5 optical density neutral density filter (#FNG 085, Melles Griot, Irvine, Calif.) and into a set of focusing optics composed of a 64 mm focal length (f.l.), 7 mm diameter positive lens and a 85 mm f.l., 5 mm diameter negative lens, resulting in a 100 µm laser spot size incident upon the capillary tube. Fluorescence emission was collected at right angles by a 12 mm f.l. 14 mm diameter aspheric collector lens and passed through a 530 nm RDF bandpass filter (Omega Optical, Inc., Brattleboro, Vt.). After the filter, the emitted light was passed through a Fabry set composed of a 48 mm f.l. 19 mm diameter aspheric Fabry lens followed by a 17 mm 10 mm diameter spherical Fabry lens. The light was then imaged on a photomultiplier tube (#R98-21, Hamamatsu, San Jose, Calif.). All of the lenses that were used for detection were manufactured by Applied Biosystems, Foster City, Calif.

A single-color sequencing "ladder" of fragments terminating at C was prepared by the dideoxy sequencing method using a sequencing kit and accompanying sequencing instructions from Applied Biosystems, Foster City, Calif. (part no. 401119, Taq Diprimer Cycle Sequencing kit). An M13mp18 DNA template (m13mp18 (+) strand, 0.1 pmole) was annealed to a fluorescent dye primer (FAM M13 (−21) primer), and primer extension was carried out using Taq polymerase, with dideoxycytidine (ddCTP) provided as 3'-terminating base. The resultant reaction mixture was stored as a dried ethanol precipitate in the dark at −20° C.

A polymer solution for resolving DNA sequencing fragments was prepared as follows. To 2.4 g urea and 0.31 g of the dried linear polyacrylamide sample from Example 1 was added 3.5 ml of a buffer consisting of 5.6 g Tris (Sigma Chemical Co.), 40 ml methanol, and 220 ml water, titrated to pH 8.0 with phosphoric acid (Tris-phosphate buffer). The mixture was stirred for about 3 hours and then filtered through a 0.45 µm pore size syringe filter. The viscosity of the solution was 180 centipoise, as measured at 37° C.

The polymer solution was loaded into the capillary tube manually via syringe. Gentle pressure on the syringe plunger was sufficient to fill the syringe with polymer solution within 60 seconds. No bubbles were observed within the filled capillary tube. Once the tube was filled, the ends of the tube were immersed in their respective anodic and cathodic reservoir solutions, which contained the same polymer solution loaded in the capillary tube.

Shortly before sample was to be loaded into the filled capillary tube, the dried sequencing reaction mixture from above was resuspended in a mixture of 5 mM aqueous EDTA (0.5 µl) and formamide (6 µl). The suspension was heated at 90° C. for 2 minutes, and then transferred to an ice bath. To load the sample into the capillary tube, the cathodic end of the tube was first washed briefly with a water squeeze-bottle to remove the droplet of polymer solution from the exterior of the tube end. The cathodic electrode and the cathodic end of the capillary tube were then placed in the sample solution, and a voltage of 6 kV was applied for 5 seconds. Separation of the sample fragments was commenced by returning the electrode and tube end to the cathodic reservoir and applying a running voltage of 12 kV. Segments of the electropherogram obtained with the sample are shown in FIGS. 2A–2E.

While the invention has been described with reference to specific methods and embodiments, it will be appreciated that various modifications and changes may be made without departing from the spirit and scope of the invention.

It is claimed:

1. In a method of determining the nucleotide sequence of a target polynucleotide, wherein DNA fragments in a DNA sequencing mixture are separated by size, the improvement comprising:

separating said DNA fragments by capillary electrophoresis in an aqueous denaturing solution comprising between 4 and 7 weight percent non-crosslinked polyacrylamide molecules having an average molecular weight of between 20 and 100 kilodaltons.

2. The method of claim 1, wherein said polyacrylamide molecules are linear polymers.

3. The method of claim 2, wherein said average molecular weight is about 55 kilodaltons.

4. The method of claim 1, which is carried out in parallel with a plurality of capillary tubes.

5. The method of claim 1, wherein by said separating, a single-base resolution is achieved for fragments of at least 300 bases in length.

6. The method of claim 1, wherein by said separating, a single-base resolution is achieved for fragments of at least 500 bases in length.

7. The method of claim 1, wherein said mixture includes two distinguishable reporters by which the 3'-terminal base in a plurality of said fragments can be identified.

8. The method of claim 1, wherein said mixture includes four distinguishable reporters for use in identifying the 3'-terminal base in a plurality of said fragments.

9. The method of claim 8, wherein said reporters are fluorescent.

10. The method of claim 1, wherein after said separating has been carried out in a capillary tube, said aqueous denaturing solution in said capillary tube is replaced with fresh aqueous denaturing solution, whereby said capillary tube is now usable for separating another polynucleotide fragment sample.

11. In a method of determining the nucleotide sequence of a target polynucleotide, which includes separating DNA fragments in a DNA sequencing mixture by size in a capillary electrophoresis tube, the improvement comprising the steps of:

(a) separating said DNA fragments by capillary electrophoresis in an aqueous solution effective to denature double stranded DNA and comprising between 4 and 7 weight percent non-crosslinked polyacrylamide molecules having an average molecular weight of between 20 and 100 kilodaltons, and (b) after said separating, removing said solution from said tube and introducing fresh aqueous denaturing solution comprising non-crosslinked polyacrylamide molecules in said tube by applying pressure to one end of said tube.

12. The method of claim 11, wherein said polyacrylamide molecules are linear polyacrylamide molecules.

13. The method of claim 12, wherein said average molecular weight is about 55 kilodaltons.

14. The method of claim 11, wherein the solution has a viscosity of between 10 and 300 centipoise at 30° C.

15. The method of claim 11, wherein by said separating, a single-base resolution is achieved for fragments of at least about 300 bases in length.

16. The method of claim 11, wherein by said separating, a single-base resolution is achieved for fragments of at least 500 bases in length.

17. The method of claim 11, carried out in parallel with a plurality of capillary tubes.

* * * * *